(12) United States Patent
Joyce et al.

(10) Patent No.: US 8,778,406 B2
(45) Date of Patent: Jul. 15, 2014

(54) ANTI-CHAFING AEROSOL POWDER

(75) Inventors: Timothy C. Joyce, Chicago, IL (US); James Hammer, Uxbridge, MA (US)

(73) Assignee: Joyce Labs, LLC, White Plains, NY (US)

( * ) Notice: Subject to any disclaimer, the term of this patent is extended or adjusted under 35 U.S.C. 154(b) by 407 days.

(21) Appl. No.: 13/206,307

(22) Filed: Aug. 9, 2011

(65) Prior Publication Data

US 2012/0039818 A1 Feb. 16, 2012

Related U.S. Application Data

(60) Provisional application No. 61/372,250, filed on Aug. 10, 2010.

(51) Int. Cl.
*A61K 33/40* (2006.01)
*A61K 31/315* (2006.01)
*A61K 9/00* (2006.01)
*A61K 9/12* (2006.01)

(52) U.S. Cl.
CPC ............. *A61K 9/0014* (2013.01); *A61K 9/0034* (2013.01); *A61K 9/0031* (2013.01); *A61K 9/12* (2013.01)
USPC .......................................... 424/614; 514/494

(58) Field of Classification Search
None
See application file for complete search history.

(56) References Cited

U.S. PATENT DOCUMENTS

| | | | |
|---|---|---|---|
| 3,088,874 A | 5/1963 | Geary et al. | |
| 4,034,077 A | 7/1977 | Hill et al. | |
| 5,098,693 A | 3/1992 | Faas, Jr. et al. | |
| 5,156,833 A | 10/1992 | Osugi et al. | |
| 2008/0260655 A1 * | 10/2008 | Tamarkin et al. | 424/45 |

* cited by examiner

*Primary Examiner* — Alton Pryor
(74) *Attorney, Agent, or Firm* — Law Office of Leo Zucker

(57) ABSTRACT

A composition and method which prevents or mitigates irritation on the skin of a subject by protecting against or relieving chafing, itching and moisture, and which provides a cooling sensation where applied.

8 Claims, No Drawings

ANTI-CHAFING AEROSOL POWDER

CROSS-REFERENCE TO RELATED APPLICATION

This application claims priority under 35 U.S.C. Sec. 119(e) of U.S. Provisional Patent Application No. 61/372,250 filed Aug. 10, 2010, titled Anti-Chafing Aerosol Powder, which is incorporated by reference in its entirety.

BACKGROUND OF THE INVENTION

1. Field of the Invention

The present invention relates to anti-irritants used to prevent, reduce or relieve chafing, and to methods of delivering such anti-irritants by way of aerosol spray canisters.

2. Discussion of the Known Art

It is known that chafing and irritation resulting in skin inflammation can result from perspiration and friction caused by rubbing of skin on skin, or of skin on articles of clothing, and that individuals often perspire the under arm, foot, groin and other areas which contributes to the chafing. Individuals apply compounds to the skin to prevent or alleviate skin inflammation, and such compounds may be applied through a variety of carriers such as gels, foam, aerosol or liquid. Examples of such compounds and their method of application are disclosed in, e.g., Hill et al., U.S. Pat. No. 4,034,077; and Fass, Jr. et al., U.S. Pat. No. 5,098,693.

Individuals also apply powders to the skin to absorb moisture which forms on the skin, and to reduce friction by providing lubricity. This in turn may eliminate skin irritation or the "itching" sensation caused by the build-up of moisture and from friction. Powders commonly used are talc or baby powder sold under the registered trademark Johnson & Johnson, and common corn starch. These powders as well as anti-inflammation compounds are commonly applied topically to exposed areas of the skin by dumping or shaking the powder onto the skin, and such powders rely primarily on gravity to reach the intended area. The compounds disclosed in the mentioned patents may be categorized as medicinal or pharmaceutical compounds, and are utilized to treat or prevent various types of actual skin inflammation or abrasion.

It is also known to apply powders by means of an aerosol spray. Examples of such methods are disclosed in, e.g., Geary et al., U.S. Pat. No. 3,088,874; and Takao et al., U.S. Pat. No. 5,156,833.

A problem exists, however, in applying a powder effectively to adhere to areas of the body that are not easily accessible by means of gravity, or are otherwise difficult to reach. This frequently entails areas at and around the groin, the buttocks, the feet and the area between the scrotum and the anus.

A further problem exists with respect to powders which cannot be applied with any precision to the target area, tend not to adhere to the skin, clump after application, and/or leave a mess on the ground or floor beneath the individual user.

A need therefore exists for a method of applying a powder onto targeted, difficult to reach areas of the skin, wherein the powder adheres to the skin, resists clumping, and does not leave a residue on the surrounding ground. Talc (or baby powder) and corn starch tend to disperse over a wide area, are affected by the slightest air movement, easily fall off the skin and leave a residue on the ground around an individual applying these compounds.

SUMMARY OF INVENTION

The present invention is directed to a novel anti-chafing mixture for specific areas of the body and which is applied preferably by use of an aerosol spray. The inventive composition and method mitigate irritation on the skin of a subject by, for example, protecting the skin, providing lubricity, relieving chafing, itching, reducing moisture and/or providing a cooling sensation where applied.

Specifically, a moisture absorbing, anti-chafing mixture of a powder blend including talc, aluminum starch octenylsuccinate and zinc oxide is delivered by an aerosol spray leaving no perceptible residue on the ground. The mixture contains lubricating and fast evaporating anti-chafing agents suspended in the carrier which also provide a cooling sensation when applied to the skin. The mixture may be applied directly to areas underneath the scrotum, between the thighs, on the underside of the buttocks and on the feet to prevent or relieve chafing and irritation. In a particular embodiment, the composition is a spray which comprises (a) zinc oxide; (b) a volatile carrier; (c) a lubricating powder blend; (d) a fast evaporating agent, (e) an aerosol propellant, and, (f) optionally menthol, and may be used to mitigate topical or skin irritation in a subject.

In a related aspect, the present invention includes method of mitigating or relieving skin irritation in a subject in need thereof by administering the above-mentioned composition to the subject in an amount effective for mitigating or relieving said skin irritation. In a particular embodiment, the composition is administered by way of an aerosol spray.

In another related aspect, the invention includes the use of: (a) talc; (b) zinc oxide; (c) a volatile carrier; (d) a fast drying, absorbent powder blend; (e) an aerosol propellant, and (f) optionally menthol in formulating a composition, particularly a spray for mitigating or relieving irritation, particularly skin irritation, and more particularly chafing in a subject.

In yet another related aspect, the invention includes the use of an aerosol spray canister to deliver the composition more precisely to a targeted area when holding the canister in either an upright or inverted orientation.

DETAILED DESCRIPTION OF THE INVENTION

A problem frequently experienced by individuals who use powder to dry their skin and reduce chafing is an inability to deliver the powder or powder composition to specific areas of the body, to target those areas, and to avoid leaving a perceptible powdery mess on the surrounding ground or floor. The present invention overcomes these problems with the use of an aerosol spray and a container which may be operated in an upright or inverted orientation.

A powder blend is carried in a rapid-drying vehicle, and delivered as an aerosol spray. The spray deposits a long-lasting powder coating to the skin, providing drying, lubricating and anti-chafing benefits, while substantially reducing the dusting produced by conventional body powders.

Where a range of values is provided, it is understood that each intervening value, to the tenth of the unit of the lower limit (unless the context clearly dictates otherwise), between the upper and lower limit of that range and any other stated or intervening value in that stated range is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although methods and materials similar or equivalent to those described herein may possibly be used in the practice or testing of the present invention, the preferred methods and materials are now described.

It is also noted that as used herein and in the appended claims, the singular forms of "a," "and", and "the", include plural references unless the context clearly dictates otherwise. Also, as defined herein, the term "mitigate" is used to mean to prevent irritation in a subject, reduce the amount of irritation in a subject, or the rate of spread of irritation.

Composition

The inventive composition comprises zinc oxide in an amount of about 0.1-5%, more preferred from about 0.1-1%, and most preferred from about 0.1-0.5%.

Additionally, the composition comprises:
1. A volatile carrier, comprised of a lower alcohol, such as ethanol or isopropanol, alone or in combination with a volatile silicone, such as hexamethyldisiloxane, cyclomethicone, or other volatile material, such as isododecane. The carrier is present in a range from about 5-20%, more preferred from about 10-15%, and most preferred from about 10-12%. The volatile silicone may represent 100% of the carrier. More preferred is about a 20/80-80/20 blend of volatile silicone with an alcohol. Most preferred is about a 55/45-65/35 blend of hexamethyldisiloxane with alcohol.
2. An absorbent powder blend. Absorbent powders are modified to produce a very large surface area and, therefore, are capable of absorbing more moisture and/or oil than conventional absorbent powders. This is achieved through a finer particle size, or through modifications which increase the porosity of the material.

For example, aluminum starch octenylsuccinate is more porous, and has more surface area than ordinary cornstarch, and can therefore absorb more moisture and/or oil. The blend may be comprised of talc, aluminum starch octenylsuccinate, sodium starch octenylsuccinate, cornstarch, tapioca starch, bentonite, kaolin, zeolite, calcium silicate, and other absorbent powders known to the art. The powder blend is present in a range from about 4-40%, more preferred from about 4-15%. Most preferred is a blend of talc and aluminum starch octenylsuccinate in a range of about 4.75-12%.

3. An aerosol propellant. Suitable propellants include, but are not limited to:
   hydrocarbons, such as n-butane, isobutane, propane; hydrofluorocarbons, such as Dymel 152a and Dymel 134a; Dimethyl ether; blends of any of the above. The propellant may be present in a range from about 30-90%, or more preferred from about 40-80%. Most preferred is n-butane in a range from about 70-80%.

Delivery System

The preferred delivery system for the inventive product is in the form of an aerosol. Most preferred is an aerosol canister fitted with a 180 or 360 degree powder spray valve system, which enables the product to be dispensed in both an upright or upside-down canister orientation.

When the mixture is applied to the target area, it prevents or mitigates chafing by absorbing moisture on the skin and adhering to the skin. Other ingredients in the mixture provide a cooling sensation to the skin. The aerosol propellants and the mixture carriers evaporate shortly after exposure to the air, leaving a fine layer of talc and zinc oxide on the skin.

The inventive delivery system overcomes a limitation of shaken powder, by suspending the talc in a medium which can be propelled laterally or vertically (with or against gravity) by way of an aerosol spray. Moreover, the suspension medium is far less affected by air currents and causes the talc to adhere to the skin for a longer lasting effect than common powder or common corn starch.

EXAMPLES

The examples set forth herein disclose various specific embodiments of the spray composition disclosed herein as well as methods of production of the spray composition.

Example 1

Fast-Drying Aerosol Body Powder Spray

| Ingredient | % |
| --- | --- |
| Zinc Oxide | 0.225 |
| SDA40B200 (alcohol) | 4.525 |
| Hexamethyldisiloxane | 5.500 |
| Isopropyl Myrsitate (IPM) | 3.750 |
| Talc | 4.750 |
| Aluminum Starch Octenylsuccinate | 4.750 |
| Magnesium Stearate | 0.750 |
| Silica | 0.500 |
| Fragrance | 0.250 |
| A-17 (n-butane) | 75.000 |
| | 100.00 |

Example 2

Fast-Drying Aerosol Body Powder Spray, with Menthol Cooling Agent

| Ingredient | % |
| --- | --- |
| Zinc Oxide | 0.225 |
| Menthol | 0.100 |
| SDA40B200 (alcohol) | 4.425 |
| Hexamethyldisiloxane | 5.500 |
| Isopropyl Myrsitate (IPM) | 3.750 |
| Talc | 4.750 |
| Aluminum Starch Octenylsuccinate | 4.750 |
| Magnesium Stearate | 0.750 |
| Silica | 0.500 |
| Fragrance | 0.250 |
| A-17 (n-butane) | 75.000 |
| | 100.00 |

Methods

The following procedure is used to obtain the sprays set forth in Examples 1 and 2.

Alcohol, hexamethyldisiloxane and isopropyl myristate are added to the mixing tank. Zinc oxide is added and mixing proceeds for approximately 5 minutes, or until homogeneous. Talc is slowly added and further mixing occurs for approximately 10 minutes, or until homogeneous. Aluminum starch octenylsuccinate is slowly added and mixed for a minimum of 30 minutes. Magnesium stearate and silica is added and mixed approximately 5 minutes until homogeneous. Fragrance and Menthol are added (where indicated), and mixing is continued for 30 minutes, or until homogeneous. Product is filled into aerosol canisters and charged with propellant, so that the product is capable of spraying with the canister upright or upside-down, and of providing a cooling sensation, increasing comfort and preventing chafing, particularly in the groin area, buttocks and feet.

Although the invention has been described with reference to specific embodiments, the details thereof are not to be construed as limiting. Further, various equivalents, changes and modifications that would be obvious to one skilled in the art are within the spirit and scope of the present invention as defined by the appended claims.

Moreover, each of the references cited throughout this specification is incorporated herein by reference in its entirety.

What is claimed is:

1. An aerosol body powder spray composition, comprising:
   (a) zinc oxide in an amount of from about 0.1% to 5% by weight;
   (b) a volatile carrier including a lower alcohol in a range of from about 5% to 20% by weight;
   (c) an absorbent and/or drying powder blend including talc and aluminum starch octenylsuccinate in a range of from about 4% to 40% by weight; and
   (d) an aerosol propellant in a range of from about 30% to 90% by weight;
   so that when the composition is applied as an aerosol body powder spray in an effective amount on the skin of a subject, the composition prevents or relieves chafing on the skin.

2. A body powder spray composition according to claim 1, including a cooling agent comprising menthol.

3. A body powder spray composition according to claim 1, wherein the volatile carrier includes a volatile silicone.

4. A body powder spray composition according to claim 1, wherein the aerosol propellant comprises n-butane.

5. A method of preventing or mitigating chafing in a subject in need thereof, comprising topically applying to the skin of said subject an effective amount of the spray composition of claim 1.

6. A method of delivering the composition of claim 1 to the skin effectively to prevent or mitigate chafing, including using the composition in the form of an aerosol spray.

7. A method of delivering the composition of claim 1 to the skin effectively to prevent or mitigate chafing of the skin in the groin, scrotum, buttocks, anus, thighs, and foot, including applying the composition in the form of an aerosol spray.

8. A method of delivering the composition of claim 1 to the skin effectively to prevent chafing of the skin in the groin, scrotum, anus, thighs, and foot, including applying the composition from an aerosol spray canister, and operating the canister in either an upright or an upside-down orientation.

\* \* \* \* \*